(12) United States Patent
Lizarazo

(10) Patent No.: US 10,209,339 B1
(45) Date of Patent: Feb. 19, 2019

(54) SELF-ADJUSTING SINGLE CONTACT VOLTAGE SENSOR

(71) Applicant: Verivolt LLC, San Francisco, CA (US)

(72) Inventor: Juan Lizarazo, Oakland, CA (US)

(73) Assignee: Verivolt Inc., San Francisco, CA (US)

( * ) Notice: Subject to any disclaimer, the term of this patent is extended or adjusted under 35 U.S.C. 154(b) by 231 days.

(21) Appl. No.: 15/216,679

(22) Filed: Jul. 21, 2016

Related U.S. Application Data

(60) Provisional application No. 62/195,477, filed on Jul. 22, 2015.

(51) Int. Cl.
  *G01R 19/00* (2006.01)
  *G01R 19/25* (2006.01)
  *G01R 35/00* (2006.01)
  *C12Q 1/6874* (2018.01)

(52) U.S. Cl.
  CPC ............. *G01R 35/00* (2013.01); *G01R 19/25* (2013.01); *C12Q 1/6874* (2013.01); *C12Q 2533/101* (2013.01); *C12Q 2565/301* (2013.01); *G01R 19/0092* (2013.01); *G01R 35/005* (2013.01)

(58) Field of Classification Search
  CPC ........ C12Q 2565/301; C12Q 2533/101; C12Q 1/6874; G01R 19/0092; G01R 35/005
  USPC ......................................................... 324/130
  See application file for complete search history.

(56) References Cited

U.S. PATENT DOCUMENTS

| | | | | |
|---|---|---|---|---|
| 4,121,154 A | | 10/1978 | Keating | |
| 5,280,239 A | * | 1/1994 | Klimovitsky | G01B 7/003 324/207.17 |
| 5,293,113 A | * | 3/1994 | Beha | G01R 19/257 324/457 |
| 5,351,532 A | * | 10/1994 | Hager | E21B 47/011 250/254 |
| 6,515,215 B1 | * | 2/2003 | Mimura | H02S 50/10 136/244 |
| 2002/0167303 A1 | * | 11/2002 | Nakano | G01R 15/16 324/126 |
| 2007/0222529 A1 | * | 9/2007 | Carichner | H03L 1/00 331/44 |
| 2008/0027586 A1 | * | 1/2008 | Hem | A01G 25/167 700/284 |
| 2010/0308852 A1 | * | 12/2010 | Unmuessig | G01R 15/16 324/750.3 |
| 2012/0176103 A1 | * | 7/2012 | Lizarazo | G01R 15/06 323/234 |

OTHER PUBLICATIONS

Sevlian, Raffi et al., Actively Calibrated Line Mountable Capacitive Voltage Transducer for Power Systems Applications, IEEE.

* cited by examiner

*Primary Examiner* — Christopher P McAndrew
(74) *Attorney, Agent, or Firm* — Intellent Patents LLC; Ahmed Alhafidh

(57) ABSTRACT

Disclosed is a voltage sensing apparatus comprising a signal generator coupled to a first conducting layer and a conductive element having a first voltage, the signal generator configured to superimpose a second voltage to the first voltage. The voltage sensing apparatus also comprises a meter disposed between the first conducting layer and a second conducting layer or between the signal generator and the second conducting layer. An output parameter of the meter is a function of one or more of the group consisting of: the first voltage and the second voltage. The output parameter and the second voltage can be used to adjust a determination of the first voltage.

21 Claims, 6 Drawing Sheets

SELF-ADJUSTING SINGLE CONTACT VOLTAGE SENSOR

CLAIM OF PRIORITY

This application claims priority to U.S. Provisional Patent Application Ser. No. 62/195,477, filed Jul. 22, 2015, the entire disclosure of which is hereby expressly incorporated by reference herein.

FIELD OF TECHNOLOGY

This disclosure relates generally to voltage sensors. More particularly, the described embodiments relate to a device, a method and/or a system for a groundless voltage sensor.

BACKGROUND

Current voltage sensors come in two varieties: conventional and groundless. Conventional voltage sensors typically connect to ground as a reference point, while groundless sensors do not. The need for a ground connection introduces a creepage path to ground through which current can flow. This path then becomes a safety hazard, and although this may be inconsequential for everyday electrical appliances where voltage is relatively low (110 V-220 V), electrical substations may carry voltages exceeding 500 kV, and this safety hazard becomes very expensive to address from an engineering perspective. Grounded voltage sensors used in such substations are large structures with numerous branches and must extend a considerable distance from the ground in order to avoid electrical breakdown (arcing), and more readily dissipate heat and prevent the risk of electrical fires and explosions. These voltage sensors are high cost, heavy, unwieldy structures that require countless man hours to install and maintain. Contrarily, groundless voltage sensors offer the benefit of a small form factor and do not introduce the safety hazard added by a creepage path where current can flow. Furthermore, groundless voltage sensors are relatively easy to install and maintain. However, current groundless voltage sensors are inaccurate, and in that respect they are more of a voltage estimator, than an actual metering tool. Furthermore, since groundless voltage sensors use infinity as a reference point, in reality, their ability to accurately measure voltage is heavily deprecated by external electrical fields (e.g. from neighboring power lines or other electrical equipment), calibration difficulties, background noise, etc.

SUMMARY

In one aspect, a voltage sensing apparatus comprises a signal generator coupled to a first conducting layer and a conductive element, the conductive element having a first voltage. The first conducting layer is separated from the conductive element by an insulating layer. The signal generator is adapted to superimpose a second voltage to the first voltage. The voltage sensing apparatus also comprises a meter disposed between the first conducting layer and a second conducting layer or between the signal generator and the second conducting layer. An output parameter of the meter is a function of one or more of the group consisting of: the first voltage and the second voltage. The second conducting layer substantially surrounds a portion of the first conducting layer.

In another aspect, a method of voltage sensing comprises applying, through a signal generator coupled to a first conducting layer and a conductive element having a first voltage, a second voltage to the first voltage. The first conducting layer is separate from the conductive element by an insulating layer. The method of voltage sensing also comprises outputting a parameter being a function of one or more of the group consisting of: the first voltage and the second voltage. The meter is disposed between the first conducting layer and a second conducting layer or between the signal generator and the second conducting layer. The second conducting layer substantially surrounds the first conducting layer.

BRIEF DESCRIPTION OF THE DRAWINGS

The embodiments of this invention are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Example embodiments, as described below, may be used to provide a device, a method and/or a system for a groundless voltage sensor.

Figure 1A:
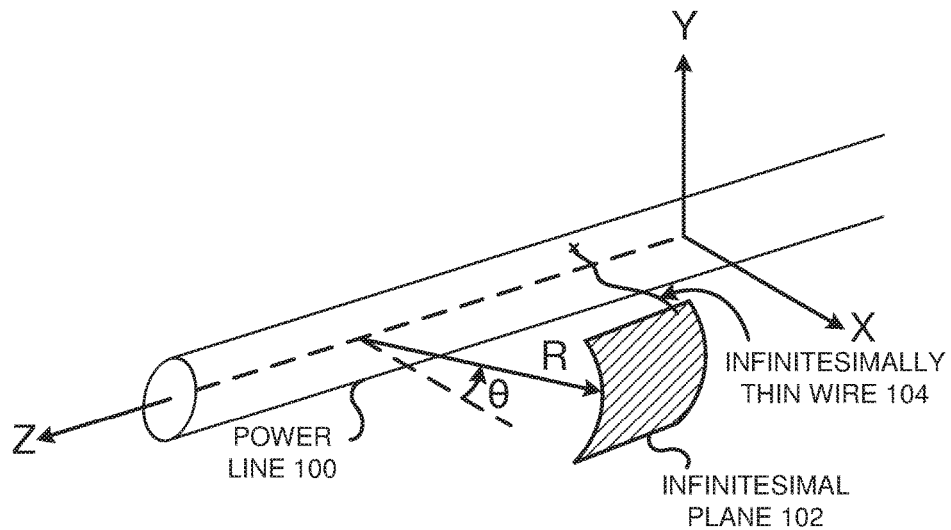
FIG. 1A is a conceptual illustration of a sensing principle used to measure voltage of a power line, according to one or more embodiments.

Reference is now made to FIG. 1A, which illustrates a sensing principle used to measure voltage of a power line. A power line 100 may have a voltage ($V_L$). The power line 100 may be coupled to an infinitesimal plane 102 through an infinitesimally thin wire 104, the infinitesimal plane 102 is a distance R from the power line 100. The infinitesimal plane 102 may be a rectangular segment of a cylinder concentric with the power line 100. The infinitesimally thin wire 104 may connect the power line 100 to the infinitesimal plane 102, thus maintaining the infinitesimal plane 102 at the same potential than the power line 100. Charge may flow from the power line 100 to the infinitesimal plane 102 through the infinitesimally thin wire 104 due to one or more of the following: $V_L$ changes, an external field appears/changes, or a new element in the surrounding environment may appear/change which may capacitively couple to the infinitesimal plane 102. For example, a tall delivery truck may park on a street right below where a sensor is mounted. From an electric perspective, the metal structure of the truck brings the ground closer to the sensor, and in this way increases the amount of charge that the source must pump into the power line to ensure that the power line is seated at a given potential. This increase in charge may be induced on the infinitesimal plane 102. Charge flowing into the infinitesimal plane 102 due to an infinitesimal change in $V_L$ can be quantified by the following equation:

$$d\partial Q = d\alpha \cdot \partial V_L \quad \text{(Equation 1.1)},$$

where Q represents the total charge induced on the infinitesimal plane 102. $d\alpha$ is a proportionality factor that depends on the geometry and material properties of the scenario and is of infinitesimal value since the infinitesimal plane 102 is infinitesimally small. Integrating Equation 1.1 yields:

$$dQ = d\alpha \cdot V_L + d\beta \quad \text{(Equation 1.2)}.$$

In Equation 1.2, $d\beta$ is a constant resulting from the integration over $V_L$ of Equation 1.1. The derivative over $V_L$ in Equation 1.1 is a partial derivative, thus, $d\beta$ is not an absolute constant, but only a constant as a function of $V_L$. $d\beta$ is a function of the geometry and material properties of the scenario, and also a function dependent on external electric fields. On the other hand, $d\alpha$ is only a function of the geometry and material properties of the scenario, but does not depend on external electric fields. This last conclusion results from applying the principle of superposition to the fields generated by different charged elements.

Figure 1B:
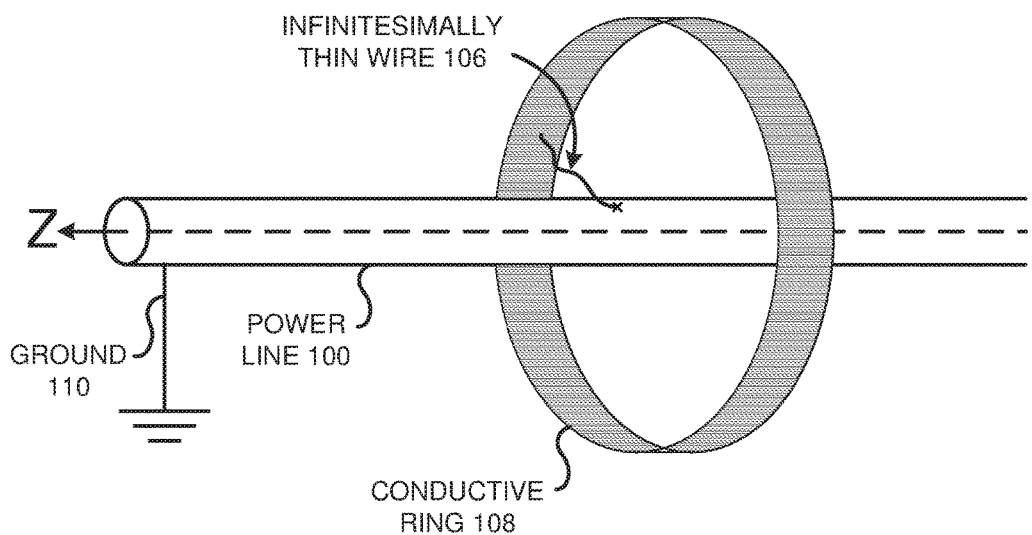
FIG. 1B is an illustration of a conductive ring encircling the power line of FIG. 1A, according to one or more embodiments.

Reference is now made to FIG. 1B, which illustrates a conductive ring encircling the power line 100 of FIG. 1A, according to one or more embodiments. The conductive ring 108 may be coupled to the power line 100 by an infinitesimally thin wire 106. The conductive ring 108 geometry may be achieved by integrating Equation 1.2 over the Z-axis and θ, using cylindrical coordinates. The charge induced on the conductive ring 108 based on $V_L$ is given by Equation 1.3 below:

$$Q = \alpha \cdot V_L + \beta \quad \text{(Equation 1.3)},$$

where α is a parameter that depends on the geometry and properties of the environment around the conductive ring 108. In other words, a is a measurement of the capacitive coupling of the conductive ring 108 to the rest of the universe. As such, a may change if elements of the surrounding environment change. To understand the meaning of β, let's consider what happens when the power line 100 is shorted to ground 110. Equation 1.3 yields:

$$Q = \beta \quad \text{(Equation 1.4)}.$$

If no external electric fields are present (such as at infinity), no charge would accumulate on the conductive ring 108 and thus β=0. Realistically, forces from external electric fields may cause charge to flow into the conductive ring 108 despite the fact that the conductive ring 108 is at ground potential. Applied to FIG. 1B, Equation 1.4 quantifies the amount of charge induced on the conductive ring 108 by the surrounding environment when the power line 100 is fixed to ground 110. Like α, β depends on the geometry of the surrounding environment. However, β additionally depends on external electric fields. External electric fields may be created by neighboring power lines or other electrical equipment in the surrounding environment of the conductive ring 108.

In realistic conditions, Q depends on parameters α and β. Though the main contribution to Q is given by the term $\alpha \cdot V_L$ as shown in Equation 1.3, in order to accurately measure $V_L$ at any moment in time, both α and β must be measured in real-time. However, the effect of β must be largely ignored since the electric fields that it depends on can have any shape and can change quickly over time. For practical purposes, β behaves as a random variable with unknown distributions and correlations to measurable variables.

Figure 2:
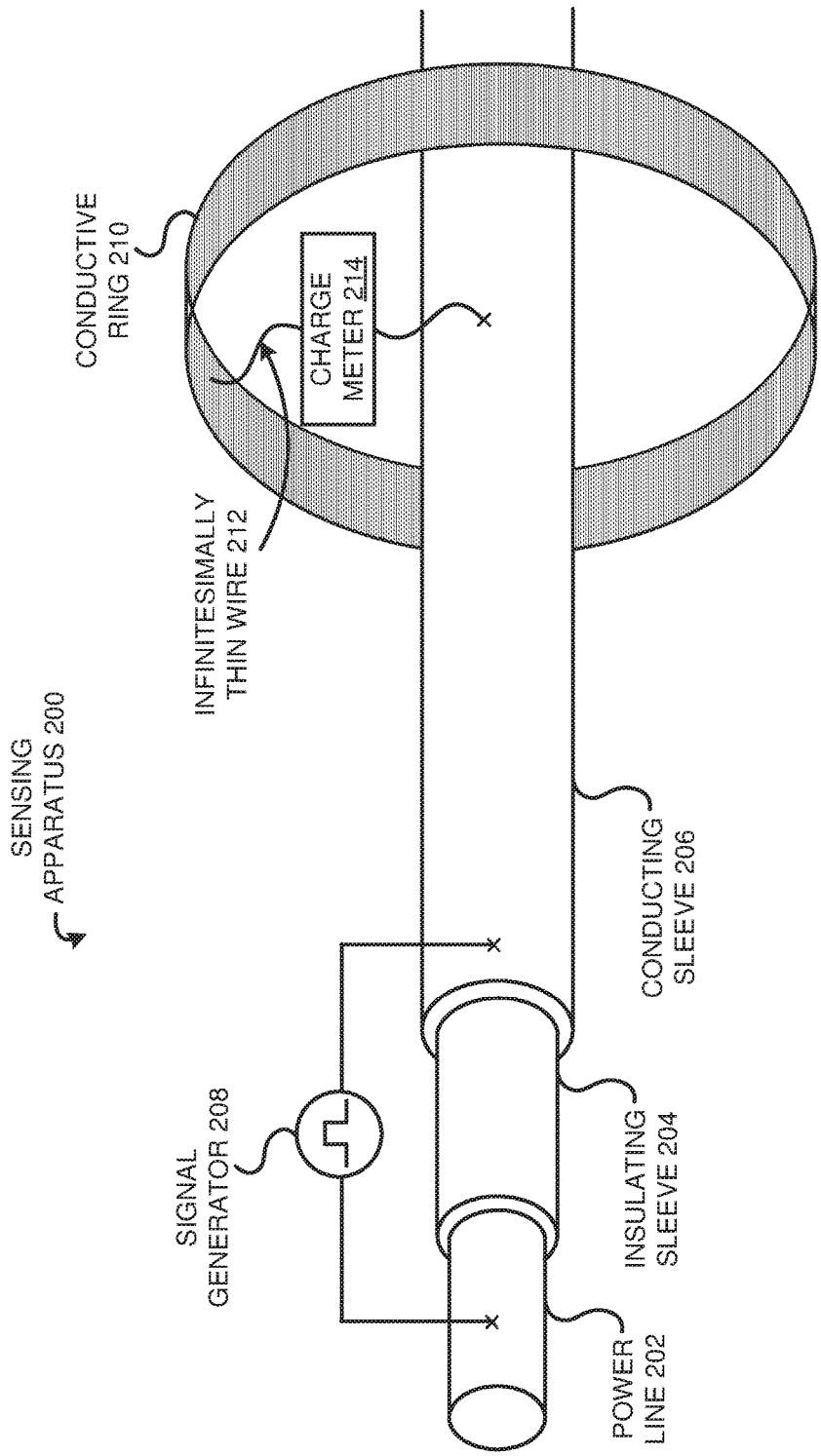
FIG. 2 is a schematic diagram of a sensing apparatus configured to measure a charge induced on the conductive ring of FIG. 1B, according to one or more embodiments.

Reference is now made to FIG. 2, which illustrates a sensing apparatus 200 configured to measure an extra charge induced on the conductive ring of FIG. 1B, according to one or more embodiments. The sensing apparatus 200 may demonstrate a method of measuring a in Equation 1.3 below:

$$Q = \alpha \cdot V_L + \beta \quad \text{(Equation 1.3)}.$$

In one embodiment, the sensing apparatus 200 may comprise a power line 202, the surface of which may be covered by an insulating sleeve 204. The insulating sleeve 204 may be subsequently covered by a conducting sleeve 206. The insulating sleeve 204 may insulate the power line 202 from the conducting sleeve 206. The power line 202 and the conductive sleeve 206 may be coupled in series with a signal generator 208. The signal generator 208 may inject a voltage signal, thus adding a known difference in potential between the power line 202 and the conducting sleeve 206. As in FIG. 1B, the sensing apparatus 200 further comprises a conductive ring 210. The conductive ring 210 may be coupled to the conducting sleeve 206 through an infinitesimally thin wire 212. A charge meter 214 circuit may be in series with the infinitesimally thin wire 212 and may measure an amount of charge flowing into the conductive ring 210. The charge meter 214 may also be any kind of meter, including but not limited to: a current meter (to measure current flowing to the conductive ring 210), a voltage meter (to measure a change in voltage induced on the conductive ring 210), or a resistor and temperature meter.

In one embodiment, a method of measuring α in Equation 1.3 above may comprise injecting a voltage signal of a known magnitude between the power line 202 and the conducting sleeve 206 through the signal generator 208. The method may further comprise measuring, through the charge meter 214, an extra charge induced on the conductive ring 210 by the voltage signal. α may be a ratio between the extra charge induced on the conductive ring 210 to the voltage signal applied to the conductive sleeve 206. However, using such a method to measure α may lead to inaccurate measurements due to several reasons.

Figure 3A:
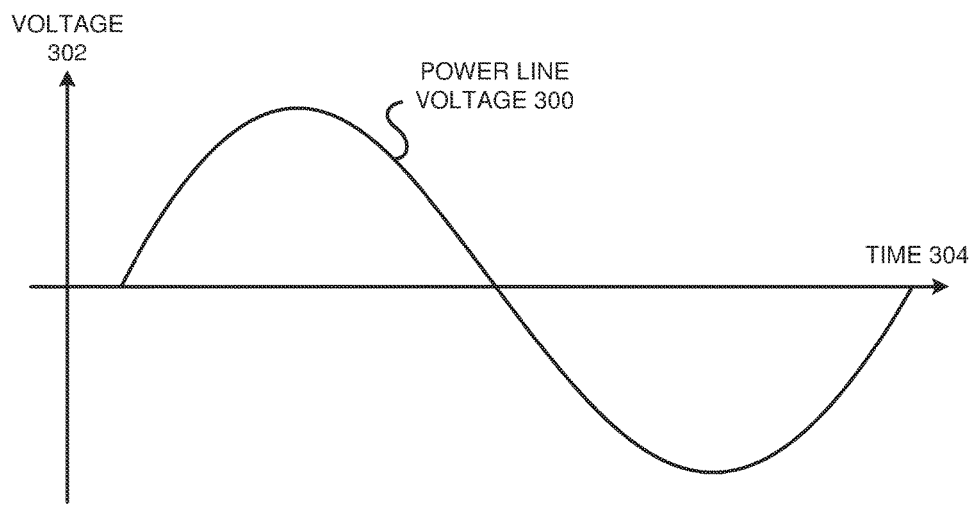
FIG. 3A is a graph illustrating a typical signal shape of the power line of FIG. 1A, according to one or more embodiments.

Reference is now made to FIG. 3A which is a graph illustrating a typical signal shape of the power line 100 of FIG. 1A, according to one or more embodiments. The power line voltage 300 is a graphic representation of the voltage 302 of the power line 202 with respect to time 304. The power line 202 may be a high voltage, low frequency power line carrying electricity that, for example, may power a city.

Figure 3B:
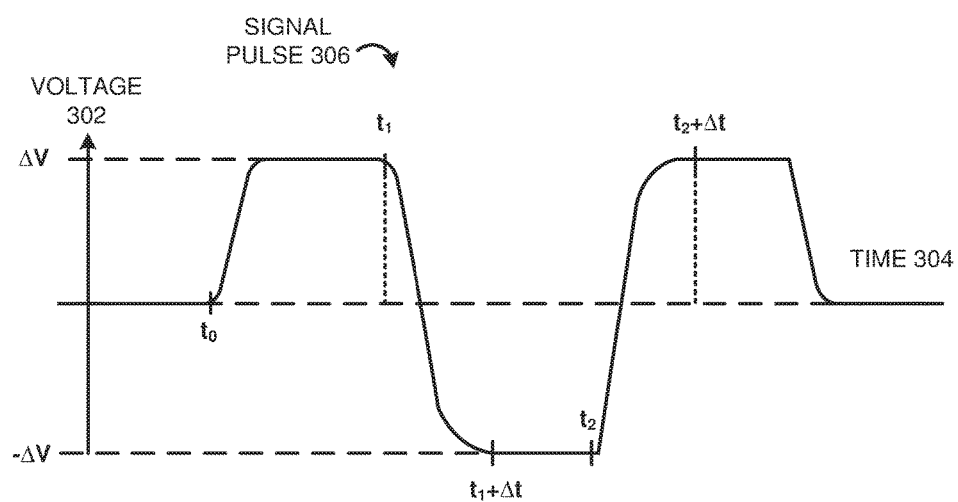
FIG. 3B is a graph illustrating a possible signal shape of a signal pulse induced on the conductive ring by the sensing apparatus of FIG. 2, according to one or more embodiments.

Reference is now made to FIG. 3B, which is a graph illustrating a possible signal shape of a signal pulse induced on the conductive ring 210 by the sensing apparatus 200 of FIG. 2, according to one or more embodiments. The signal pulse 306 may be a graphical visualization of the extra charge and may graph a change in voltage 302 over time 304 induced on the conductive ring 210 by the signal generator 208 of the sensing apparatus 200. At $t=t_0$, the voltage from the signal generator 208 is $V_G=0$. A step voltage may be applied and at $t=t_1$, the voltage is $V_G=\Delta V$. At $t=t_1$, the polarity of the signal generator 208 may reverse, and at time $t=t_1+\Delta t$, the voltage is $V_G=-\Delta V$. At $t=t_2$, the polarity of the signal generator 208 reverses again and the voltage becomes $V_G=\Delta V$ at $t=t_2-\Delta t$. At $t=t_3$, the voltage from the signal generator 208 returns to $V_G=0$. Applying the signal pulse 306 to the conductive sleeve 206 through the signal generator 208 will cause the voltage of the conductive sleeve 206 to deviate by the amount shown in FIG. 3B. The signal pulse 306 may be a low voltage, high frequency voltage signal.

Figure 3C:
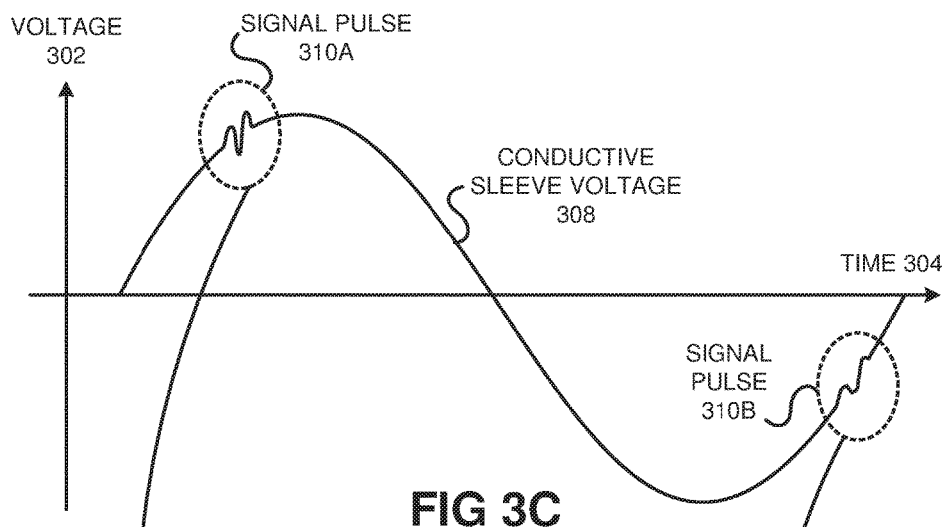
FIG. 3C is a graph illustrating the signal shape of the conductive sleeve after the signal pulse of FIG. 3B is induced on the conductive ring by the signal generator of FIG. 2, according to one or more embodiments.

Summing the signal pulse 306 and the power line voltage 300 may yield FIG. 3C, which is a graph illustrating the signal shape of the conductive sleeve 206 after the signal pulse 306 of FIG. 3B is induced on the conductive sleeve 206 by the signal generator 208 of FIG. 2, according to one or more embodiments. The conductive sleeve voltage 308 is shown as a function of time 304. Additionally, the conductive sleeve voltage 308 exhibits a signal pulse 310A and a signal pulse 310B, both of which are induced by the signal generator 208 of the sensing apparatus 200 of FIG. 2. Signal pulse 310A may be induced on the conductive sleeve 206 at a time at which a slope of the conductive sleeve voltage 308 (and by extension, the power line voltage 300) is relatively low. Signal pulse 310B may be induced on the conductive sleeve 206 a time at which a slope of the conductive sleeve voltage 308 (and by extension, the power line voltage 300) is relatively high.

Figure 3D:
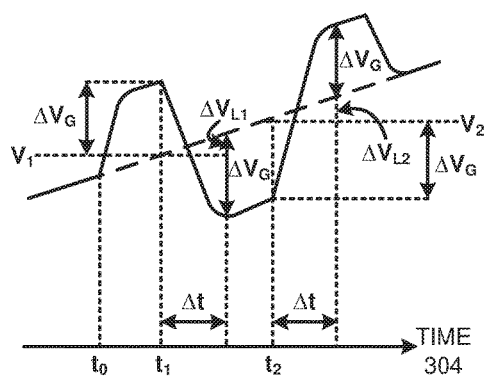
FIG. 3D is a signal graph detail of a signal pulse of FIG. 3C at which the change in slope of the conductive sleeve voltage is relatively low, according to one or more embodiments.

Reference is now made to FIG. 3D, which shows graph detail of the signal pulse 310A of FIG. 3C, at which the change in slope of the conductive sleeve voltage 308 is relatively low, according to one or more embodiments. Referencing Equation 1.3 above, the change in the charge on the conductive ring 210 of the sensing apparatus 200 from $t=t_1$ to $t=t_1+\Delta t$ is given by $$\Delta Q_1 = \alpha \cdot (V_1 + \Delta V_{L1} - \Delta V_G) - \alpha \cdot (V_1 + \Delta V_G) = \alpha \cdot (\Delta V_{L1} - 2 \cdot \Delta V_G)$$ (Equation 3.1).

The change in the charge on the conductive ring 210 of the sensing apparatus 200 from $t=t_2$ to $t=t_2+\Delta t$ is given by $$\Delta Q_2 = \alpha \cdot (V_2 + \Delta V_{L2} + \Delta V_G) - \alpha \cdot (V_2 - \Delta V_G) = \alpha \cdot (\Delta V_{L2} + 2 \cdot \Delta V_G)$$ (Equation 3.2).

$V_1$ and $V_2$ are the voltage of the power line 202 at times $t_1$ and $t_2$ respectively. $\Delta V_{L1}$ and $\Delta V_{L2}$ are the change on the voltage of the power line 202 going from $t_1$ to $t_1+\Delta t$, and going from $t_2$ to $t_2+\Delta t$, respectively. $\Delta V_G$ is the size of the step voltage induced by the signal generator 208. If the signal pulse 310A from signal generator 208 is sufficiently fast such that $\Delta V_G$ is larger than $\Delta V_{L1}$ and $\Delta V_{L2}$, then $\Delta Q_1$ will be negative and $\Delta Q_2$ will be positive. This is expected, as the induced voltages at $t_1$ and $t_2$ are of opposite polarity.

Subtracting Equation 3.1 from Equation 3.2 yields $$\Delta Q_2 - \Delta Q_1 = 4 \cdot \alpha \cdot \Delta V_G + \alpha \cdot (\Delta V_{L2} - \Delta V_{L1})$$ (Equation 3.3).

Averaging multiple signal pulses 310A yields $$\langle \Delta Q_2 - \Delta Q_1 \rangle = 4 \cdot \alpha \cdot \Delta V_G + \alpha \cdot \langle \Delta V_{L2} - \Delta V_{L1} \rangle$$ (Equation 3.4).

Focusing on the term $\langle \Delta V_{L2} - \Delta V_{L1} \rangle$, $\Delta V_{L2}$ represents the change in the power line voltage 300 from $t_2$ to $t_2+\Delta t$ and $\Delta V_{L1}$ represents the change in the power line voltage 300 from $t_1$ to $t_1+\Delta t$. Before averaging, $(\Delta V_{L2} - \Delta V_{L1})$ can be rewritten as $$\Delta V_{L2} - \Delta V_{L1} = \Delta t \cdot \left( \frac{\Delta V_{L2}}{\Delta t} - \frac{\Delta V_{L1}}{\Delta t} \right) = \Delta t \cdot (m_2 - m_1)$$ (Equation 3.5)

where $m_1$ and $m_2$ are the slopes of the voltage 302 as a function of time 304 (i.e. dV/dt) at $t_1$ and $t_2$, respectively. Since the change in slope at signal pulse 310A is higher than that of signal pulse 310B, the value of $\Delta V_{L2} - \Delta V_{L1}$ will be relatively larger.

Figure 3E:
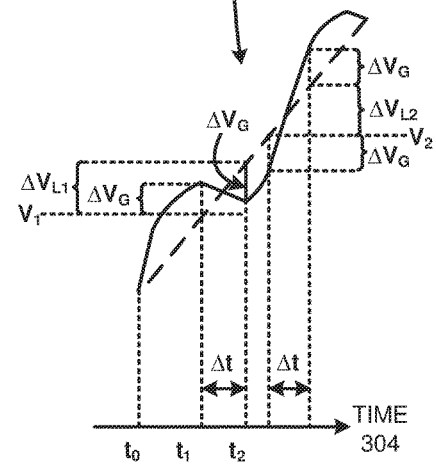
FIG. 3E is a signal graph detail of a signal pulse of FIG. 3C at which the change in slope of the conductive sleeve voltage is relatively high, according to one or more embodiments.

Reference is now made to FIG. 3E which shows graph detail of the signal pulse 310B of FIG. 3C at which the change in slope of the conductive sleeve voltage 308 is relatively high, according to one or more embodiments. Using the same calculations above in Equation 3.1-3.4, $(\Delta V_{L2} - \Delta V_{L1})$ may yield a smaller number since the change in slope at signal pulse 310B is lower than the change of slope for signal pulse 310A. The error in the calculation of $(\Delta V_{L2} - \Delta V_{L1})$ is maximized at the peak of the power line voltage and eliminated when the power line voltage crosses the zero point.

Two ways to reduce the magnitude of $(\Delta V_{L2} - \Delta V_{L1})$ are to reduce the time length of the signal pulse generated by signal generator 208 and to switch the polarity of signal generator 208 very fast.

By reducing the time length of the signal pulse, the change in slope $(m_2 - m_1)$ would be reduced. This is already shown in FIG. 3C, since the period of the signal pulse 310A is very small compared to the period of a cycle of the conductive sleeve voltage 308 (and by extension, the power line voltage 300). As a result, the change on dV/dt through the length of the signal pulse 310A is very small, making $(m_2 - m_1)$ very small. In other words, although the conductive sleeve voltage 308 may change a lot from $t_1$ to $t_2$ (as the conductive sleeve voltage 308 during signal pulse 310B), there is a negligible change on the rate-of-change of the conductive sleeve voltage 308 between $t_1$ to $t_2$ due to the high frequency of signal pulse 310A. The maximum change on the rate-of-change of the conductive sleeve voltage 308 occurs at the peaks, but at the peaks, the slope dives to zero. (Subtracting or adding two small numbers would still yield a small number).

By using a signal generator 208 that can switch polarity very fast, $\Delta t$ can be made very small, further reducing the size of the overall expression on the right side of Equation 3.5.

Although the above two methods reduce the magnitude (and thus, the effect) of $(\Delta V_{L2} - \Delta V_{L1})$, taking an average over multiple signal pulses is what cancels out the effect of the change of the power line voltage 300 in our measurement of $\alpha$. Using a large sample size of signal pulses, the term $\langle \Delta V_{L2} - \Delta V_{L1} \rangle$ becomes equal to zero. This is because for a sampling scheme not synchronized with the power line voltage 300, the contributing terms are equally likely to be positive or negative with equal amplitudes. Solving for $\alpha$ in Equation 3.4 and averaging enough samples to make $\langle \Delta V_{L2} - \Delta V_{L1} \rangle$ converge to zero, we have:

$$\alpha = \frac{\langle \Delta Q_2 - \Delta Q_1 \rangle}{4 \cdot \Delta V_G},$$ (Equation 3.6)

where $\Delta Q_1$ and $\Delta Q_2$ are quantities measured by the charge meter 214 of the sensing apparatus 200 of FIG. 2.

In one embodiment, a method of operating the sensing apparatus 200 of FIG. 2 to measure $\alpha$ may be to operate the sensing apparatus in either a calibration mode or a measurement mode. In the calibration mode, the signal generator 208 of the sensing apparatus 200 may apply a series of signal pulses or a sinusoidal wave at a given frequency. The charge meter 214 may collect charge data that may be used to calculate parameter α. In the measurement mode, the signal generator 208 may act as a short ($V_G=0$) and the parameter α previously calculated in the calibration mode may be used to obtain the voltage of the power line 202 based on the total charge generated by the signal generator 208 and sensed by the charge meter 214.

In another embodiment, a real-time calibration method may be implemented in which the signal generator of the sensing apparatus 200 periodically injects signal pulses, and the parameter α may be corrected by a small amount after each signal pulse until the value of parameter α converges. As such, the sensing apparatus 200 may remain in measurement mode, and the data points used to calculate the parameter α may then be acquired together with the data points used to determine the voltage of the power line 202.

Figure 4:
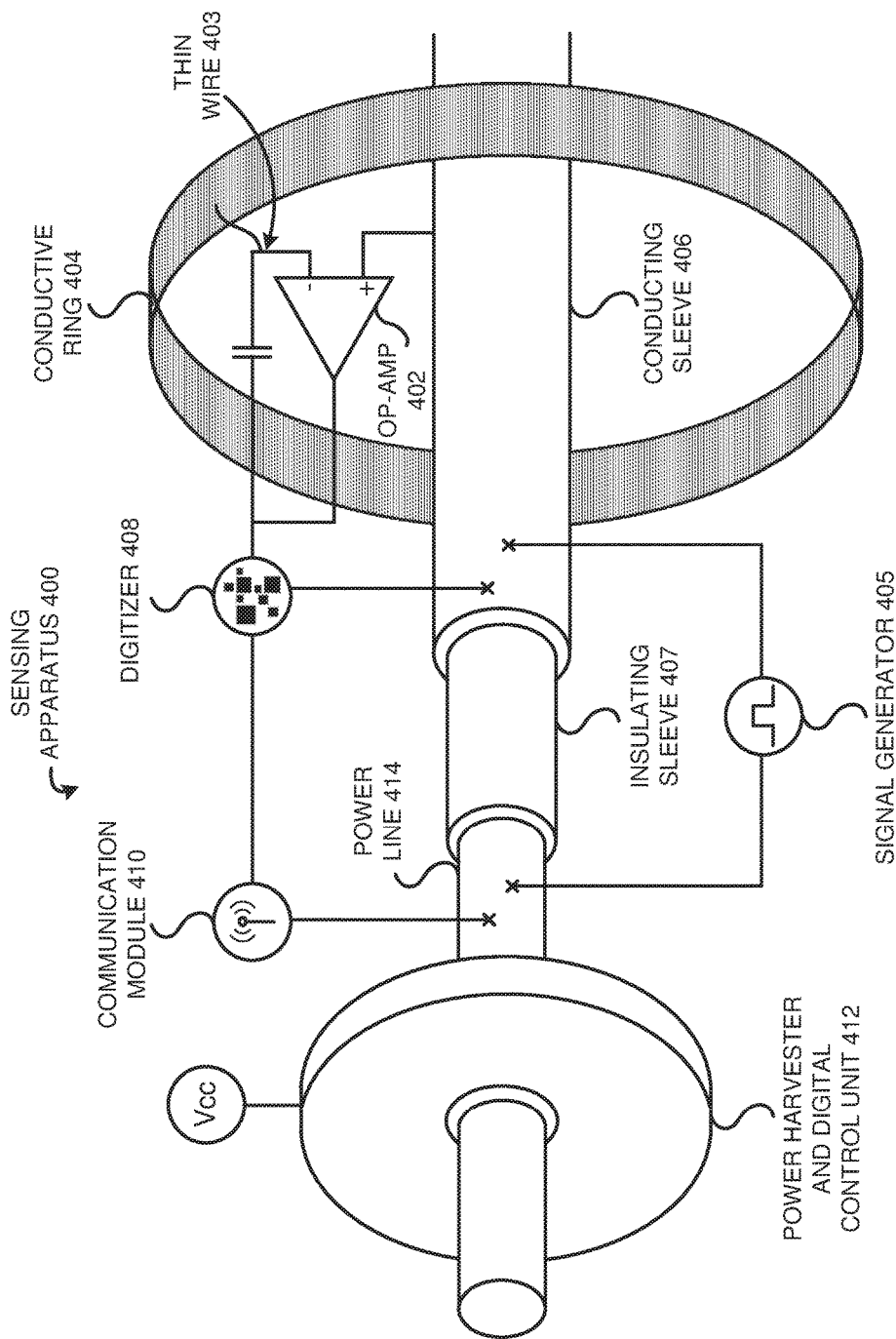
FIG. 4 is a schematic diagram of the sensing apparatus of FIG. 2 comprising a facility for real-time calibration and communication to a ground-based computer, according to one or more embodiments.

Reference is now made to FIG. 4, which is a schematic diagram of a sensing apparatus 400 comprising a facility for real-time calibration and communication to a ground-based computer, according to one or more embodiments. The charge meter 214 may comprise an operational amplifier (op-amp) 402 in an integrator configuration, which may provide the charge necessary to maintain the potential of the conductive ring 404 at the same level as the conducting sleeve 406 and may output a voltage proportional to the charge accumulated in the conductive ring 404. The output of the op-amp 402 may be fed to a digitizer 408. For example, the digitizer 408 may be an off-the-shelf cRio digitizer. Alternately, the digitizer 408 may be a dedicated integrated circuit (IC) comprising an analog to digital converter (ADC) chip. The output of the digitizer 408 may feed into a communication module 410. The communication module 410 may provide a means by which the sensing apparatus 400 may communicatively couple to a data processing device. The communicative coupling may be wireless and may be achieved through the use of any wireless protocols. Alternately, the communicative coupling may be achieved through an optical data cable. For example, data output from the digitizer 408 may be communicated to the data processing device through an optical data cable. Alternately, data may be transmitted wirelessly through WiFi, Bluetooth, NFC, or through cellular data networks (GSM, CDMA, etc.). Other communication means and protocols are within the scope of the exemplary embodiments described herein. The data processing device may receive the digitized data from the digitizer 408 and may subsequently perform computations based on the digitized data. The sensing apparatus 400 may further comprise a power harvester and digital control unit 412 that may harvest power from the power line 414, which may be used to power the components of the sensing apparatus 400. This unit may also have any necessary control I/O needed to synchronize the different elements in the sensing apparatus 400. All of the components of the sensing apparatus 400 described herein are mounted on top of the power line 414. As such, the components of the sensing apparatus 400 are seated at the potential of the power line 414. For this reason, wireless or optical communicative couplings are utilized to transfer data from the digitizer 408 and the data processing device.

The sensing apparatus 400 may provide a means for real-time calibration and measurement of the parameter α. However, in practical situations where voltage is very high, the number of samples required to average the term $\langle \Delta V_{L2} - \Delta V_{L1} \rangle$ increases steeply with the voltage to be measured. For example, a power line may transmit 500 kV at 60 Hz. The signal generator may utilize a sinusoidal calibration signal with a frequency of 20 kHz and a peak voltage of 10V. Let's estimate the number of samples needed to make $\langle \Delta V_{L2} - \Delta V_{L1} \rangle$ negligible compared to $4 \cdot \Delta V_G$ in Equation 3.4.

The period of the sinusoidal calibration signal will be:

$$t_2 - t_1 = \Delta t = (\tfrac{1}{2}) \cdot (\tfrac{1}{20} \text{ kHz}) = 25 \mu s$$

$\Delta V_{L1}$ is the change in the power line voltage from $t_1$ to $t_1 + \Delta t$ and $\Delta V_{L2}$ is the change in the power line voltage from $t_2$ to $t_2 + \Delta t$. For the power line voltage, we have:

$$V_L(t) = A \cdot \text{Sin}(w \cdot t) \quad \text{(Equation 4.1)},$$

where A=500 kV, and w=2·π·60 Hz. To simplify the calculation, let's call $t_0 = t_1 + \Delta t$. Thus:

$$\Delta V_{L2} - \Delta V_{L1} = A \cdot [\text{Sin}(w(t_0 + \Delta t)) - \text{Sin}(wt_0)] - A \cdot [\text{Sin}(wt_0) - \text{Sin}(w(t_0 - \Delta t))] \quad \text{(Equation 4.2)}$$

$$\Delta V_{L2} - \Delta V_{L1} = -2A \cdot \text{Sin}(wt_0) \cdot [1 - \text{Cos}(w\Delta t)] \quad \text{(Equation 4.3)}$$

Equation 4.3 tells us that the maximum error will occur when $\text{Sin}(wt_0) = \pm 1$. Thus:

$$|\Delta V_{L2} - \Delta V_{L1}|_{MAX} = 2A \cdot [1 - \text{Cos}(w\Delta t)] \quad \text{(Equation 4.4)}$$

For a 500 kV power line at 60 Hz, using a 20 kHz calibration signal, the maximum error is 22V. In Equation 3.4, the term related to the effect of the calibration signal is $4 \cdot \Delta V_G = 40V$. In order to achieve a 0.1% accuracy when measuring the parameter α, enough samples must be average such that $\langle \Delta V_{L2} - \Delta V_{L1} \rangle \leq 40$ mV. Using Equation 4.4 and assuming a flat distribution of samples from −22V to 22V, we have that in order to achieve 0.1% accuracy, we would need 100 k samples. Since we obtain a sample for every cycle of the 20 kHz calibration signal, it would take 5 seconds to collect around 100 k samples.

Although the result is feasible in practical situations, there are other contributing sources of error: the digitization error of the digitizer, the signal-to-noise ratio (SNR) of the digitizer, and the noise of the power line itself. Assuming a 16-bit digitizer over a full 500 kV range, the charge induced by the 10V calibration signal (ΔQ) will receive only 1 bit of resolution. The use of 16-bit digitizers is widely prevalent in the industry and is a cost-effective middle ground. As such, the use of higher-bit digitizers may not be feasible for everyday deployment. However, improvements to the sensing apparatus 400 may be introduced to reduce the number of samples needed by 1) increasing the resolution of the digitizer, 2) improving the SNR of the digitizer, and 3) reducing the noise of the power line.

Figure 5:
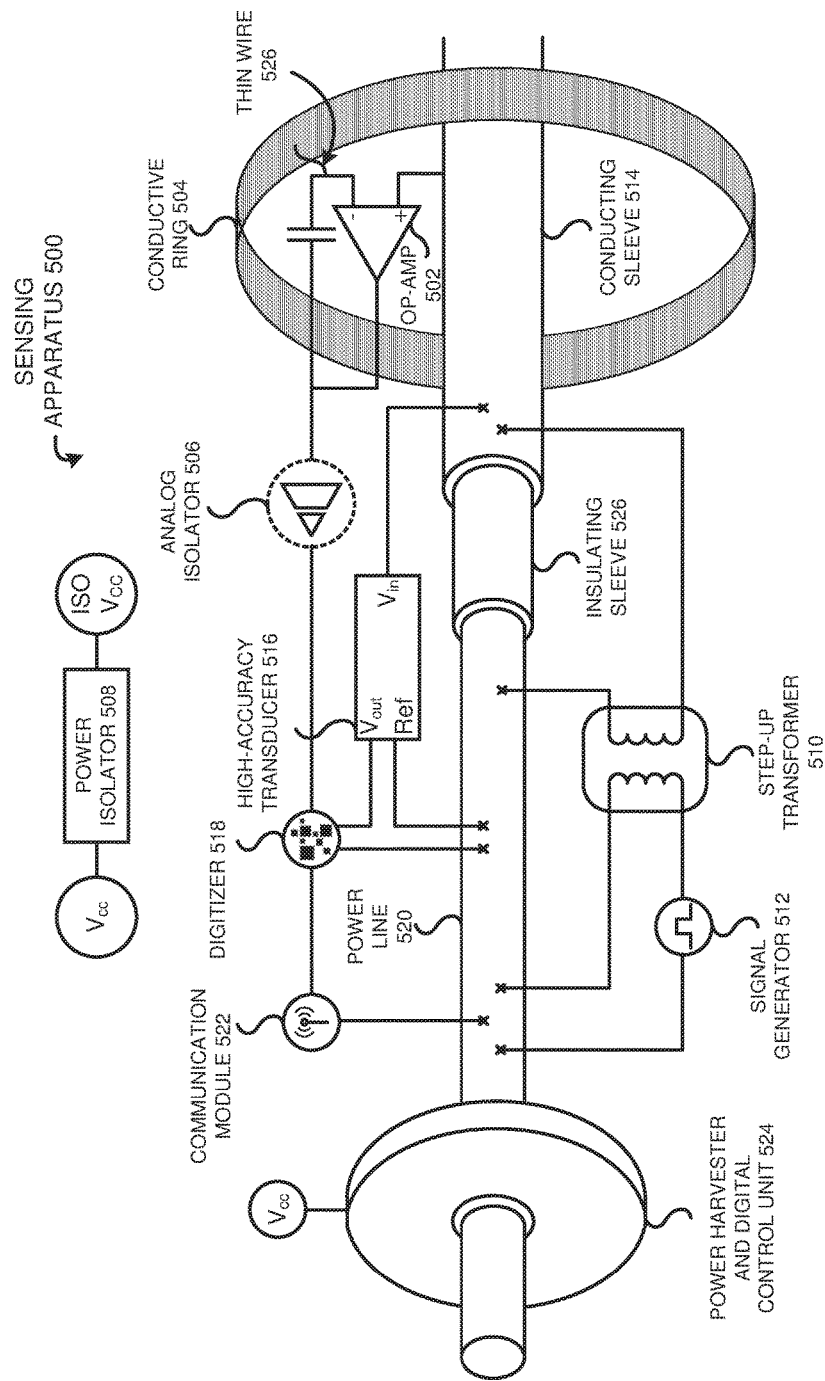
FIG. 5 is a schematic diagram of the sensing apparatus of FIG. 4 configured to isolate the conducting sleeve and the conducting ring from the rest of the apparatus, according to one or more embodiments.

Reference is now made to FIG. 5, which is a schematic diagram of the sensing apparatus of FIG. 4 configured to isolate the conducting sleeve and the conducting ring from the rest of the apparatus, according to one or more embodiments. The introduction of low-level isolation allows the usage of a bigger calibration signal. The signal from the op-amp 502 that charges the conductive ring 504 may be isolated by an analog isolator 506. Furthermore, the power being fed into the op-amp 502 may be isolated by a power isolator 508. Additionally, a step-up transformer 510 may be connected between the output of the signal generator 512 and the conducting sleeve 514. A high-accuracy transducer 516 may be connected to the conductive sleeve 514 to scale down the voltage from the conducting sleeve 514 and feed the scaled down voltage into a digitizer 518.

The sensing apparatus 500 isolates the conducting sleeve 514 and the op-amp 502 from the rest of the sensing apparatus 500. The analog isolator 506 may be an IC such as a AMC1200 (made by Texas Instruments) and the power isolator 508 may be any isolated DC-to-DC converter. With this isolation, the effective calibration signal applied to the conducting sleeve 514 may be a higher value than the standard 10V typically used for low voltage electronics.

The low side of the step-up transformer 510 may connect between the output of the signal generator 512 and the power line 520. The high side of the step-up transformer 510 may connect between the conducting sleeve 514 and the power line 520. Using this configuration, the output of the step-up transformer 510 will then be the calibration signal ($V_G$ as in FIG. 3B), with an amplitude 10 to 100 times greater than sensing apparatus 400. Under a practical scenario, this may amount to having a calibration signal of 100V to 1000V. The high-accuracy transducer 516 may be used to measure the voltage of the conducting sleeve 514 ($V_{in}$) with respect to the power line 520 (Ref). This facilitates an increase in accuracy by measuring the signal $V_G$ being induced on the conducting sleeve 514 by the signal generator 512 (rather than using the nominal value by design), and using the measured value ($V_{out}$) to calculate parameter α. As such, Equation 3.6 becomes $$\alpha = \frac{\langle \Delta Q_2 - \Delta Q_1 \rangle}{4 \cdot \langle \Delta V_G \rangle} \quad \text{(Equation 5.1)}$$

where $V_G$ is included as an averaged value rather than a fixed value. For every sample collected, the change in charge ($\Delta Q_2 - \Delta Q_1$) is measured together with the change in voltage $V_G$. This stream of values would then be used to calibrate α.

Although the present embodiments have been described with reference to specific example embodiments, it will be evident that various modifications and changes may be made to these embodiments without departing from the broader spirit and scope of the various embodiments. For example, the various devices and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structure and methods may be embodied using transistors, logic gates, and electrical circuits (e.g., application specific integrated (ASIC) circuitry and/or Digital Signal Processor (DSP) circuitry).

In addition, it will be appreciated that the various operations, processes and methods disclosed herein may be embodied in a non-transitory machine-readable medium and/or a machine-accessible medium compatible with a data processing system. Accordingly, the specification and drawings are to be regarded in an illustrative rather than a restrictive sense.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system or digital control unit), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

What is claimed is:

1. A voltage sensing apparatus, comprising:
a signal generator coupled to a first conducting layer and a conductive element, the conductive element comprising a power line, the conductive element having a first voltage,
wherein the first conducting layer is separated from the conductive element by an insulating layer,
wherein the signal generator is adapted to superimpose a second voltage to the first voltage;
a meter disposed between the first conducting layer and a second conducting layer or between the signal generator and the second conducting layer, an output parameter of the meter being a function of one or more of the group consisting of: the first voltage and the second voltage,
wherein the second conducting layer substantially surrounds a portion of the first conducting layer,
wherein the output parameter accounts for a charge accumulated by the second conducting layer from an environment surrounding the first conducting layer.

2. The apparatus of claim 1, wherein the output parameter and the second voltage can be used to adjust a determination of the first voltage.

3. The apparatus of claim 1, wherein the meter is a charge meter adapted to measure a change in charge induced on the second conducting layer.

4. The apparatus of claim 1, wherein the meter is a voltage meter adapted to measure a change in voltage induced on the second conducting layer.

5. The apparatus of claim 1, wherein the meter is a current meter adapted to measure current flow into the second conducting layer.

6. The apparatus of claim 1, wherein in a calibration mode, the signal generator applies the second voltage as a series of signal pulses or a sinusoidal wave at a given frequency.

7. The apparatus of claim 1, wherein in a measurement mode, the signal generator shorts to allow a measurement of the first voltage based on a previous calculation that uses the output parameter to the second voltage.

8. The apparatus of claim 1, wherein the meter outputs a voltage that could be used to reconstruct the first voltage, or the voltage of the second conducting layer.

9. The apparatus of claim 7, further comprising:
an analog-to-digital converter adapted to convert the output voltage to a digital format.

10. The apparatus of claim 1, further comprising:
a battery or a power harvester adapted to provide power to the components of the voltage sensing apparatus.

11. The apparatus of claim 1, further comprising an isolator adapted to isolate the application of the second voltage.

12. The apparatus of claim 10, further comprising an isolator adapted to isolate the power being fed into the meter.

13. The apparatus of claim 1, further comprising:
a means for amplifying the second voltage applied by the signal generator, said means being disposed between the signal generator and the second conducting layer.

14. The apparatus of claim 1, further comprising:
a transducer to scale down a voltage of the second conducting layer and output the scaled down voltage to an analog-to-digital converter.

15. The apparatus of claim 9, further comprising:
a communications module communicatively coupled to the analog-to-digital converter, the communications module adapted to enable transmission of measured or calculated data.

16. A method of voltage sensing comprising:
applying, through a signal generator coupled to a first conducting layer and a conductive element having a first voltage, a second voltage to the first voltage,
wherein the first conducting layer is separated from the conductive element by an insulating layer; outputting, through a meter disposed between the first conducting layer and a second conducting layer or between the signal generator and the second conducting layer, a parameter being a function of one or more of the group consisting of: the first voltage and the second voltage, wherein the second conducting layer substantially surrounds the first conducting layer
wherein the output parameter accounts for a charge accumulated by the second conducting layer from an environment surrounding the first conducting layer.

17. The method of claim 16, further comprising:
calculating the first voltage through a digital control unit coupled to the meter based on the parameter and the second voltage.

18. The method of claim 16, wherein the second voltage is applied as a series of signal pulses or a sinusoidal wave at a given frequency.

19. The method of claim 16, further comprising:
measuring, through the digital control unit, a voltage of the conductive element based on a previous calculation of the output parameter to the applied second voltage.

20. The method of claim 16, wherein the meter outputs a voltage proportional to a voltage of the second conducting layer.

21. The method of claim 16, further comprising:
scaling down, through a transducer, a voltage of the second conducting layer to be output to an analog-to-digital converter.

* * * * *